(12) United States Patent
Neuberger

(10) Patent No.: US 7,018,397 B2
(45) Date of Patent: Mar. 28, 2006

(54) FLEXIBLE DEVICE FOR TOPICAL APPLICATION OF PDT

(75) Inventor: Wolfgang Neuberger, F.T. Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 165 days.

(21) Appl. No.: 10/255,803

(22) Filed: Sep. 25, 2002

(65) Prior Publication Data
US 2004/0059399 A1    Mar. 25, 2004

(51) Int. Cl.
*A61N 5/06* (2006.01)

(52) U.S. Cl. .............. 607/91; 607/88; 607/89; 606/9; 606/17; 606/23

(58) Field of Classification Search ............ 606/2, 606/8, 9, 13, 16–18, 22, 23; 607/88–91
See application file for complete search history.

(56) References Cited

U.S. PATENT DOCUMENTS

| | | | |
|---|---|---|---|
| 5,309,925 A | | 5/1994 | Policastro |
| 5,505,726 A | * | 4/1996 | Meserol .................. 606/9 |
| 6,096,066 A | * | 8/2000 | Chen et al. .............. 607/88 |
| 6,231,593 B1 | | 5/2001 | Meserol |

* cited by examiner

*Primary Examiner*—A. Farah
(74) *Attorney, Agent, or Firm*—BJ Associates; Bolesh J. Skutnik

(57) ABSTRACT

A waveguide and radiation delivery system is disclosed to be used in topical applications of photodynamic therapy. One preferred embodiment consists of a rectangular waveguide that delivers electromagnetic radiation to a flexible conducting sheet that can be molded to the contours of the treatment sight. The sheet is surrounded by a reflective material or foil, except for the portion of the sheet in contact with the treatment area. That portion is covered with a semi-reflective sheet that is at least translucent with respect to the wavelength used in the treatment. This invention increases the speed and efficiency of the procedure by reducing energy loss due to reflection from the skin surface. It also increases safety by protecting sensitive areas of the body, and is particularly useful for head and neck procedures. Other embodiments include the use of a bladder-type applicator or a rectangular applicator designed to keep the optical fiber a specified distance from the treatment site.

15 Claims, 2 Drawing Sheets

FLEXIBLE DEVICE FOR TOPICAL APPLICATION OF PDT

BACKGROUND OF THE INVENTION

1. Field of the Invention

The invention concerns electromagnetic delivery systems for use of photodynamic therapy in topical applications.

2. Information Disclosure Statement

Photodynamic Therapy is a relatively new use for electromagnetic radiation in fighting disease. Photodynamic therapy involves the use of light to activate certain pharmaceuticals, known as photosensitizing agents, that are generally injected into the body. Exposure to electromagnetic radiation activates the molecules in these drugs, inducing them to kill cancerous cells in the body.

This promising technique is especially useful because it is relatively non-invasive, quick, and is accomplished with reduced side-effects associated with other cancer treatments such as chemotherapy. It can also work to kill cancer cells without causing significant damage to healthy tissue in the body.

The first step in photodynamic therapy is to introduce cancer-killing photosensitizing agents into the body, either orally or by injection. The agents are absorbed in cells throughout the body, but remain in cancerous cells. After a period of time, the agents remain primarily in cancerous cells, and can then be irradiated. Laser light is then applied to the areas containing cancerous cells, which activates the drugs in the tumors and kills those cells.

Because most therapeutic laser light cannot penetrate farther than a few centimeters into the body through the skin, photodynamic therapy is most often used to treat skin cancer or destroy tumors close to the skin. It is also available to treat lung cancer or esophageal cancer, where tumors are sufficiently close to oral passages so light can reach them when a fiber is inserted down the patient's airway.

For topical applications, a large portion of light aimed at the treatment area is reflected off the skin. This raises concerns as to efficiency and speed of the procedure, as well as to the safety of such procedures. Exposure to radiation used in some photodynamic therapy procedures is a concern for the patient and possibly the operator. Patients have suffered injury, especially eye injury, from exposure to laser radiation during surgical procedures. It is useful to be able to protect other areas of the body while irradiating target areas.

The prior art discloses methods for increased efficiency of radiation delivery and safety. Policastro discloses, in U.S. Pat. No. 5,309,925, a modified metallic foil used as a protective barrier in laser surgery. The foil surface is modified so as to diffuse the laser light into multiple beams to dissipate the energy of the reflected laser light. It addresses safety concerns and is offered as a method to protect patients and surgical staff from damage due to reflected laser beams. This invention is utilized as a barrier placed on the patient in areas adjacent to the treatment to protect the patient.

U.S. Pat. No. 6,231,593, by Meserol, discloses a device for using hydrogel as a means of coupling radiation to the skin in photodynamic therapy. This invention consists of a cover that houses a fiber-optic array and hydrogel for use in coupling electromagnetic energy and photopharmaceuticals. The hydrogel is also useful for softening and hydrating the stratum corneum to facilitate transmission of light and photopharmaceuticals. This invention is useful for topical treatment of dermal lesions. However, this invention is meant to be used as a patch, or a stationary cover designed to treat a specific lesion on the skin over a period of time. It is not practical for scanning over a large lesion, and may be cumbersome for treating areas of the body that are oddly shaped or otherwise not conducive to a patch.

Thus, there is a need for a protective photodynamic therapy delivery system that is movable over the treatment area, easily conformable to the contours of the treatment area, and coupled with the delivery device so as to avoid the need for separate protective equipment. The present invention fulfills this need, by disclosing a device that is simultaneously a handpiece, laser light delivery system and a protective barrier against irradiation of unintended areas of the patient's body or the medical professionals performing the procedure.

BRIEF SUMMARY OF THE INVENTION

It is an object of this invention to provide a photodynamic therapy device to increase safety during such procedures.

It is another object of this invention to provide a device that increases the speed and efficiency of photodynamic therapy procedures.

It is a further object of this invention to provide a light delivery device that can be used without further need for protective measures.

Briefly stated, the present invention consists of a waveguide and radiation delivery system to be used in topical applications of photodynamic therapy. One embodiment consists of a rectangular waveguide that delivers electromagnetic radiation to a flexible conducting sheet that can be molded to the contours of the treatment site. A reflective material or foil surrounds the sheet, apart from the portion of the sheet in contact with the treatment area. The portion of the sheet that comes in contact with the treatment area is or is covered with a semi-reflective sheet that is at least translucent with respect to the wavelength used in the treatment. This invention increases the speed and efficiency of the procedure by reducing energy loss due to reflection from the skin surface. It also increases safety by protecting sensitive areas of the body, and is particularly useful for head and neck procedures. Other embodiments include the use of a bladder-type applicator or a rectangular applicator designed to keep the optical fiber a specified distance from the treatment site.

The above, and other objects, features and advantages of the present invention will become apparent from the following description read in conjunction with the accompanying drawings, (in which like reference numbers in different drawings designate the same elements.)

BRIEF DESCRIPTION OF FIGURES

FIG. 1B—3-Dimensional picture of two variations of a preferred embodiment

FIG. 1C—3-Dimensional picture of a preferred embodiment as applied to a surface

FIG. 2B—3-Dimensional picture of a second preferred embodiment

DETAILED DESCRIPTION OF PREFERRED EMBODIMENTS

Figure 1A:
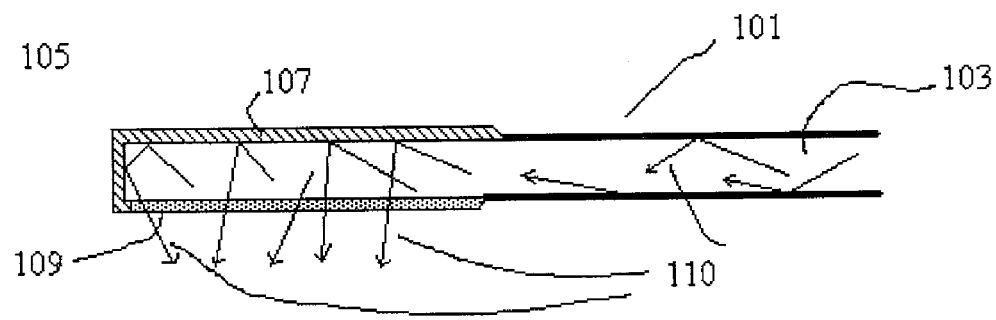
FIG. 1A—Schematic Diagram of a preferred embodiment of the present invention

A device for the application of therapeutic radiation is disclosed that both increases the safety of a radiation procedure for the patient and practitioner, and also reduces the need for inconvenient and potentially bulky safety equipment. The treatment device is especially well suited for photodynamic therapy, but may be utilized in any treatment incorporating electromagnetic radiation.

The device comprises two main parts: an optical waveguide and a conformable light conducting material for contact with the treatment site. The waveguide may be any light conducting device such as an optical fiber. In a preferred embodiment, a rectangular waveguide is utilized to produce a uniform beam over a treatment area. The conducting material has the additional feature of being transmissive to a predetermined treatment radiation wavelength for the surface area which is in contact with the treatment surface, while being non-transmissive for that area not in contact with the treatment surface. In this way, treatment radiation is permitted to travel from a radiation source and directly to the treatment site, but any treatment radiation that is directed away from the treatment site will be absorbed or reflected back within the conducting material.

In a preferred embodiment, the reflective area of the conducting material is in the form of a reflective coating on the portion of the outer surface that does not come into contact with the treatment area. In a preferred embodiment, this coating is a metallic foil. The reflectivity of the coating has the additional benefit of increasing the efficiency of the treatment by reflecting misdirected radiation back onto the treatment site. Variable coatings may be used for different purposes. In one embodiment, the foil is reflective for all radiation. In another embodiment, the foil is reflective only for the treatment radiation, allowing the user to visualize the treatment site during irradiation. In yet another embodiment, the coating is reflective for a preselected range of wavelengths that may be considered harmful.

The area that is to contact the treatment surface is preferably coated with a semi-reflective coating that transmits treatment radiation but reflects or absorbs radiation of other wavelengths. The coating may be translucent, in the case where a diffuse treatment beam is desired, or completely transparent to treatment radiation.

A further benefit of the present invention stems from the fact that the treatment radiation is transmitted directly to the treatment site through the conducting material, which allows for efficient dispersion of heat generated at the treatment site. This reduces the chances of burning the skin without the need for additional cooling means.

In some treatments, however, additional temperature control may be desired. The conducting material may also be easily cooled from the exterior of the conducting material without changing any configurations of the device. Additionally, if the conducting material consists of liquid or gel, circulation channels can be incorporated into the conducting material through the outer reflective coating to allow heated conducting material to be removed and cooler material to be introduced during treatment.

The present invention increases the speed and efficiency of treatments by reducing the amount of energy that is lost due to reflection at the skin. Radiation reflected from the skin is reflected back from the outer reflective surface and redirected back towards the treatment site. Also, because the conducting material is placed directly on the treatment site and has a higher index of refraction than air, reflection of the radiation from the material/skin interface is reduced. More radiation is thus refracted into the skin because the refractive index of the material and skin are closer in value, and this results in more efficient penetration and thus greater efficiency of treatment.

Figure 1B:
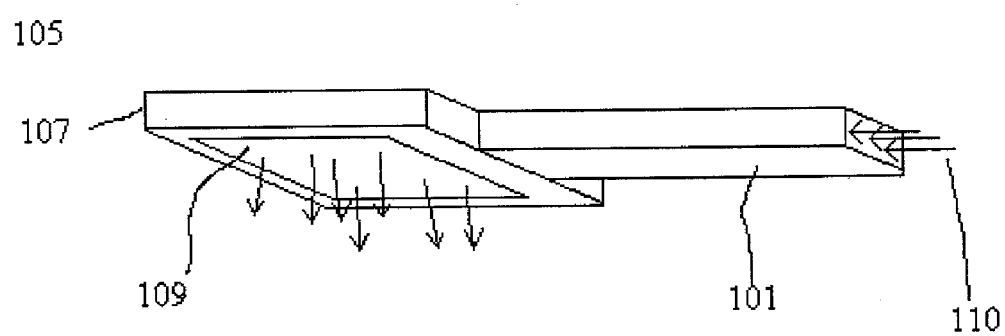
Figure 1C:
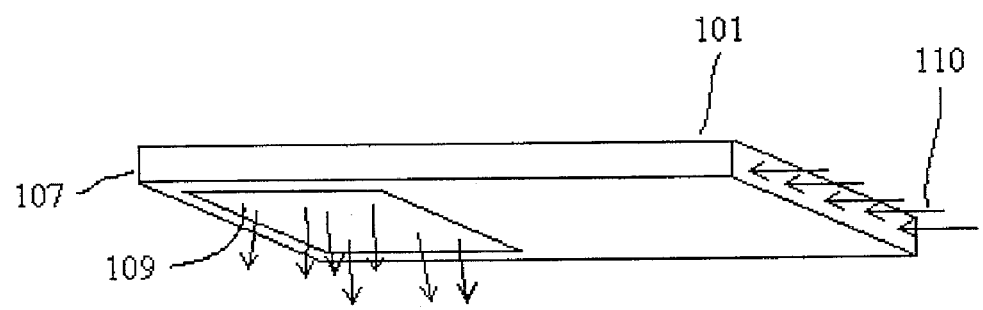

One preferred embodiment of the present invention is illustrated in FIGS. 1A, 1B and 1C. The embodiment consists of flat rectangular waveguide 101 consisting of conducting material 103. Waveguide 101 is connected to applicator 105, which is flexible and can conform its surface to match the contours of the treatment site. Applicator 105 is partially encased in reflecting foil 107. The portion of applicator that is placed in contact with the treatment area is lined with semi-reflective foil 109. Electromagnetic radiation 110 enters the waveguide, and is propagated along the waveguide, through conducting material 103 until it enters applicator, which may also consist of conducting material 103. Radiation 110 is reflected by foil 107, and is forced to exit through semi-reflected foil 109, which is formulated in such a way as to be transparent as to the desired wavelength and reflective or absorptive of undesirable or dangerous wavelengths.

This configuration allows the user to apply radiation to the treatment site while, preventing radiation from coming in contact with other areas of the patient's body or the user. This invention relieves the user of the need to apply any separate protective barriers to the patient's body or any protective gear to the user.

Figure 2A:
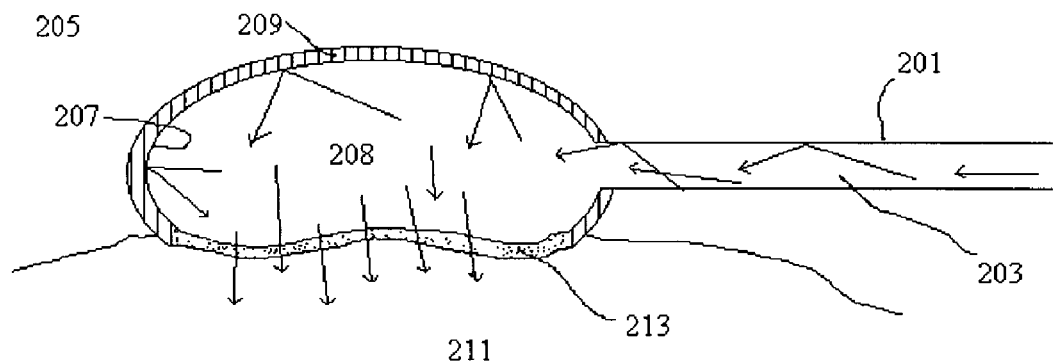
FIG. 2A—Schematic diagram of a second preferred embodiment
Figure 2B:
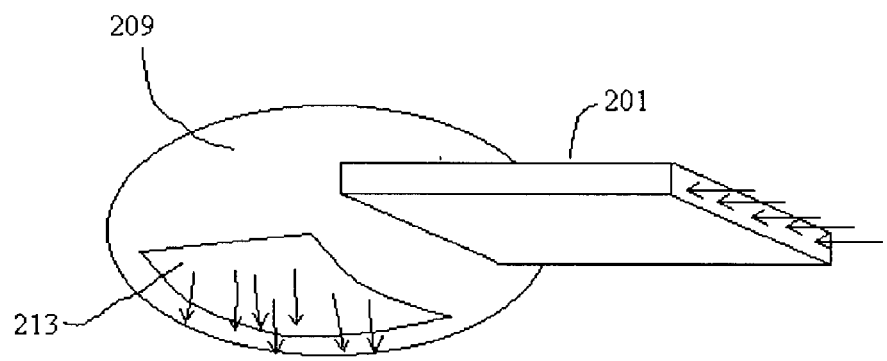

Another embodiment is illustrated in FIGS. 2A and 2B. In this embodiment, waveguide 201, containing conducting material 203, is attached to applicator 205. Applicator 205 consists of bladder 207, which is made of a transparent material. Contained within bladder 207 is conducting material 208, which may be either in gaseous, liquid or gel form. Reflective foil 209 lines a majority of the bladder, with the exception of the area of the bladder that is in contact with treatment area 211. The portion in contact with treatment area 211 is covered by semi-reflective foil 213, which is of a material that is transparent as to the desired wavelength. Applicator 205 will conform itself to the shape of the treatment area providing a seal between semi-reflective foil 213 and treatment area 211, thus preventing the escape of any undesirable radiation.

In another embodiment, the optical fiber or other waveguide is incorporated into a flexible solid block that may be rectangular. In this embodiment, the waveguide can be maintained in contact with the conducting material so that radiation is emitted at a specified distance and/or angle relative to the treatment site.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A device for photodynamic therapy of tissue, comprising:
    a. a radiation source;
    b. a flexible electromagnetic radiation conducting material capable of conforming to the contours of a treatment site, wherein said material has a portion of its surface that is adapted to contact with said treatment site and a portion of its surface that is not in contact with said treatment site;

c. wherein said portion that is adapted to contact with said treatment site is at least translucent to a treatment wavelength, wherein said portion that is not in contact with said treatment site is not translucent to said treatment wavelength; and d. a waveguide connecting said radiation source and said conducting material in said portions, said waveguide also containing said conducting material.

2. The device according to claim 1, wherein said portion that is adapted to contact with said treatment site is transparent.

3. The device according to claim 1, wherein said portion that is not in contact with said treatment site is covered with a reflective coating/foil.

4. The device according to claim 3, wherein said reflective coating/foil is reflective to certain wavelengths chosen from a group consisting of all wavelengths, wavelengths that are known to be harmful to personnel, and wavelengths being used in the treatment.

5. The device according to claim 1, wherein said portion that is adapted to contact with said treatment site is covered with a semi-reflective coating/foil.

6. The device according to claim 5, wherein said semi-reflective coating/foil is transparent with respect to electromagnetic radiation having a wavelength used on said treatment site.

7. The device according to claim 1, wherein said waveguide is rectangular.

8. The device according to claim 1, wherein said conducting material is a flexible sheet that can be molded to conform to the contours of a treatment surface.

9. The device according to claim 1, wherein said flexible conducting material is encased in a flexible bladder.

10. The device according to claim 9, wherein said bladder, when pressed against the treatment surface, will conform to the contours of the surface of said treatment site.

11. The device according to claim 9 wherein said bladder is transparent.

12. The device according to claim 9, wherein said conducting material is transparent and is in a form chosen from a group consisting of liquid, air, gas and gel.

13. A device for photodynamic therapy of tissue, comprising:

a. a radiation source;

b. a flexible electromagnetic radiation conducting material capable of conforming to the contours of a treatment site, wherein said material has a portion of its surface that is adapted to contact with said treatment site and a portion of its surface that is not in contact with said treatment site, wherein said flexible conducting material is transparent and is in a form chosen from a group consisting of liquid, air, gas and gel; said flexible conducting material being encased in a flexible bladder;

c. wherein said portion that is adapted to contact with said treatment site is at least translucent to a treatment wavelength, wherein said portion that is not in contact with said treatment site is not translucent to said treatment wavelength;

d. a waveguide connecting said radiation source and said conducting material; and e. a cooling means.

14. The device according to claim 13, wherein said cooling means comprise channels for circulating said conducting material.

15. A device for photodynamic therapy of tissue, comprising:

a. a radiation source;

b. a flexible electromagnetic radiation conducting material capable of conforming to the contours of a treatment site, wherein said material has a portion of its surface that is adapted to contact with said treatment site and a portion of its surface that is not in contact with said treatment site;

c. wherein said portion that is adapted to contact with said treatment site is at least translucent to a treatment wavelength, wherein said portion that is not in contact with said treatment site is not translucent to said treatment wavelength;

d. a waveguide connecting said radiation source and said conducting material; and e. a cooling means.

* * * * *